United States Patent [19]
Hu

[11] Patent Number: 6,162,459
[45] Date of Patent: *Dec. 19, 2000

[54] ACYCLOVIR TRANSDERMAL DELIVERY SYSTEM

[75] Inventor: Oliver Yoa-Pu Hu, Taipei, Taiwan

[73] Assignee: National Science Council, Taipei, Taiwan

[*] Notice: This patent issued on a continued prosecution application filed under 37 CFR 1.53(d), and is subject to the twenty year patent term provisions of 35 U.S.C. 154(a)(2).

[21] Appl. No.: 08/801,885

[22] Filed: Feb. 18, 1997

Related U.S. Application Data

[62] Division of application No. 08/394,114, Feb. 24, 1995, abandoned.

[51] Int. Cl.[7] .............................. A61K 9/70; A61F 13/00; A61F 13/02; A61L 15/16
[52] U.S. Cl. .......................... 424/449; 424/447; 424/448
[58] Field of Search .................................. 424/447, 448, 424/449

[56] References Cited

U.S. PATENT DOCUMENTS

| | | | |
|---|---|---|---|
| 4,879,376 | 11/1989 | Foresta et al. | 536/18.1 |
| 5,079,252 | 1/1992 | Beauchamp | 514/262 |
| 5,733,572 | 3/1998 | Unger et al. | 424/450 |

OTHER PUBLICATIONS

The Merck Index, Susan Budavari, ed., 11th edition, 1989, p. 1079.

*Primary Examiner*—Thurman K. Page
*Assistant Examiner*—T. Ware
*Attorney, Agent, or Firm*—W. Wayne Liauh

[57] ABSTRACT

A transdermal formulation for providing antiviral effect in dermis or epidermis, wherein comprising (a) 0.01 to 30 weight percent of antiviral drug; (b) 0.05 to 20 weight percent of a Chinese medicine enhancer; and (c) a pharmaceutical acceptable vehicles. The antiviral drug is selected from the group consisting of ACV(Acyclovir), Carbovir, DDA(2',3'-Dideoxyadnosine), HPMPA(1-(3-Hydroxy-2-phosphonylmethoxylpropyl)-adenosine), DHPG (Ganciclovir), Desciclovir, IDC (5-Iodo-2'-deoxy-cytidine), Vidarabine(Ara-A), DDI(2',3'-Dideoxyinosine), Cordycepin, Cytarabine, Deoxyguanosine, d4T(2',3'-Didehydro-3'-deoxythymidine), FIAC(2'-Fluoro-5-iodoaracytosine), AZT(ZDV, Zidovudine), Ara-T(1-β-D-Ara-binofuranosylthymine), Deoxythymidine, Ribavirin, EDU(5-Ethyl-2'-deoxy-uridine), Enviroxime, Amantadine, Arildone, HPMPC(9-(3-Hydroxy-2-phosphonyl-methoxyl-propyl)cytidine), Riboxamide, Rimantidine, Tromantadine, Foscamet sodium, Moroxydine, F3T(5-Trifluoro-methyl-2'-deoxy-uridine), BVDU (Bromovinyldeoxyuridine). Preferably, the Chinese medicine enhancer is oleanolic acid, and the pharmaceutical acceptable vehicles is polyethylene glycols.

2 Claims, 17 Drawing Sheets

FIG. 1-1

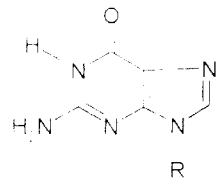

|  |  | R: |
|---|---|---|
| D 1 | Acyclovir | (2-Hydroxyethoxy)methyl |
| D 2 | Ganciclovir | (1,3-Dihydroxy-2-propoxy-methyl) |
| D 5 | Carbovir | Carbocyclic 2',3'-didehydro-2',3'-dideoxy |
| D 9 | Deoxyguanosine |  |

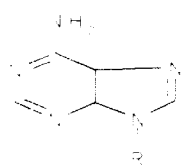

|  |  | R: |
|---|---|---|
| D 4 | Vidarabine | D-arabinofuranosyl |
| D 6 | 2',3'-Dideoxyadnosine | 2',3'-Dideoxy-9-beta-ribofuranosyl |
| D 8 | Cordycepin | 9-cordyceposido |

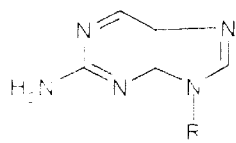

|  |  | R: |
|---|---|---|
| D 3 | Desciclovir | methoxy ethanol |

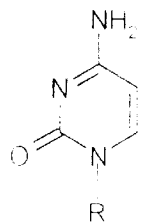

|  |  | R: |
|---|---|---|
| D11 | Cytarabine | 1-beta-D-arabinofuranosyl |
| D12 | 2',3'-Dideoxy-cytidine | 2',3'-Dideoxy-4-amino-1-beta-D-ribofuranosyl |
| D17 | 2'-Fluoro-5-iodoaracytosine | 2'-Fluoro-5-iodo-4-amino-1-beta-D-arabinofuranosyl |
| D18 | 5-Iodo-2'-deoxycytidine | 2'-Deoxy-5-iodo-4-amino-1-beta-D-ribofuranosyl |

FIG. 1-2

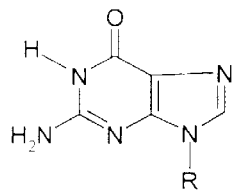

|     |                      | R:                                  |
|-----|----------------------|-------------------------------------|
| D 1 | Acyclovir            | (2-Hydroxyethoxy)methyl             |
| D 2 | Ganciclovir          | (1,3-Dihydroxy-2-propoxy-methyl)    |
| D 5 | Carbovir             | Carbocyclic 2',3'-didehydro-2',3'-dideoxy |
| D 9 | Deoxyguanosine       |                                     |

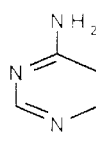

|     |                      | R:                                  |
|-----|----------------------|-------------------------------------|
| D 4 | Vidarabine           | D-arabinofuranosyl                  |
| D 6 | 2',3'-Dideoxyadnosine | 2',3'-Dideoxy-9-beta-ribofuranosyl |
| D 8 | Cordycepin           | 9-cordyceposido                     |

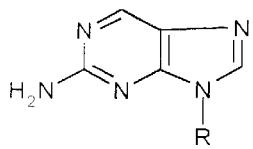

|     |             | R:             |
|-----|-------------|----------------|
| D 3 | Desciclovir | methoxy ethanol |

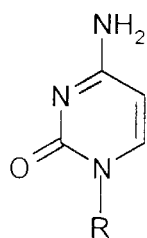

|     |                              | R:                                          |
|-----|------------------------------|---------------------------------------------|
| D11 | Cytarabine                   | 1-beta-D-arabinofuranosyl                   |
| D12 | 2',3'-Dideoxy-cytidine       | 2',3'-Dideoxy-4-amino-1-beta-D-ribofuranosyl |
| D17 | 2'-Fluoro-5-iodoaracytosine  | 2'-Fluoro-5-iodo-4-amino-1-beta-D-arabinofuranosyl |
| D18 | 5-Iodo-2'-deoxycytidine      | 2'-Deoxy-5-iodo-4-amino-1-beta-D-ribofuranosyl |

FIG. 1-3

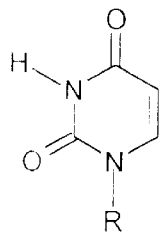

| | | R: |
|---|---|---|
| D13 | Zidovudine | 1-(3-Azido-2,3-dideoxy-β-D-erythro-pentofuranosyl) |
| D14 | 2',3'-Didehydro-2',3'-deoxythymidine | 1-(2,3-didehydro-3-deoxy-β-D-erythro-pentofurano- |
| D15 | Deoxythymidine | |
| D16 | Bromovinyl-deoxyuridine | 5-(2-Bromovinyl)-2'-deoxy |
| D19 | Deoxyuridine | 1-(2-deoxy-beta-D-erythro-pentofuranosyl |
| D20 | 5-Trifluoromethyl-2'-deoxyuridine | |

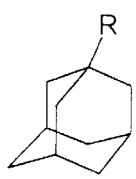

| | | R: |
|---|---|---|
| D25 | Amantidine | amine |
| D26 | Rimantidine | methyl-methanamine |
| D27 | Tromantadine | [2-(dimethylamino)ethoxy] acetamide |

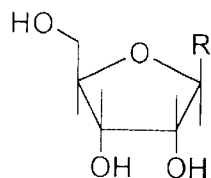

| | | R: |
|---|---|---|
| D23 | Ribavirin | 1,2,4-triazole-3-carboxamide |
| D24 | Riboxamide | thiazolcaboxamide |

FIG. 1-4

D28  Arildone          4-[6-(2-Chloro-4-methoxyphenoxy)hexyl]
                       3,5-heptane-"dione D29  Moroxydine        N-(Aminoiminomethyl)-4-morpholine-
                       carboximid-Bioxine D30  Enviroxime        6-[(Hydroxyimino)phenylmethyl]-1-[(
                       1-methylethyl) sulfonyl]-(1H)-benzimidazol-2-amine D31  Foscarnet sodium  Dihydroxyphosphinecarboxylic acid
                       oxide trisodium

ACYCLOVIR TRANSDERMAL DELIVERY SYSTEM

This application is a Division of Ser. No. 08/394,114 filed Feb. 24, 1995 now abandoned.

TECHNICAL FIELD OF THE INVENTION

The present invention relates to a topical formulation, especially to shown highly antiviral effect in dermis or epidermis.

BACKGROUND OF THE INVENTION

Viruses have caused a great stir in this century. Disease attributed to them such as HSV-1, hepatitis, HIV and AIDS are incurable. Antiviral drug that are in current use could be classified as antipurines, antipyrimidines, antibiotics, natural alkaloids, and enzymes which include Acyclovir (ACV, D1), 9-(1,3-Dihydroxy-2-propoxymethyl) guanine(Ganciclovir, D2, DHPG), Desciclovir(D3), 9-β-D-arabinofuranosyl-9H-purin-6-amine(Vidarabine, Ara-A, D4), 2',3'-Dideoxyadnosine (2',3'-Dideoxy-9-β-ribofuranosyl-9H-purine-6-amine, DDA, D6), Carbovir(D5),2',3'-Dideoxyinosine(DDI, D7), 1-(3-Hydroxy-2-phosphonylmethoxylpropyl) -adenosine (HPMPA, D10), Cordycepin(D8), Deoxyguanosine(D9), Cytarabine(D11), 3'-Azido-3'-deoxythymidine(Zidovudine, AZT, ZDV, D13), 2', 3'-Didehydro-3'-deoxythymidine(d4t, D14), 5-Iodo-2'-deoxy-cytidine(IDC, D18), Deoxythymidine(D15), 2'-Fluoro-5-iodo-aracytosine (FIAC, D17), Bromovinyldeoxyuridine (BVDU, D16), 1-β-D-Arabinofuranosyl thymine(Ara-T, D21), 9-(3-Hydroxy-2-phosphonylmethoxylpropyl)cytidine (HPMPC, D22), 5-Ethyl-$2^1$-deoxyuridine(EDU, D19), 5-Trifluoro-methyl-2'-deoxy-uridine(F3T, D20), Ribavirin(D23), Riboxamide (D24), Amantadine(D25), Arildone(D28), Rimantidine (D26), Foscamet sodium(D31), Tromantadine(D27), Moroxydine(D29), Enviroxime (D30), and as listed in table 1. They are usually administered orally, topically or parenterally. Their known serious side effects have included central nervous system toxicities and renal dysfunctions.

Structurally, as shown in FIG. 1. ACV(D1) is an analogy of deoxyguanosine with an acyclic carbohydrate moiety. It is active agonist HSV 1, HSV 2, Varicella Zoster virus (VZV), Epstein Barr virus(EBV), and Cytomegalovirus (CMV), especially HSV 1. In vivo studies rated ACV better than FIAC(D17) and DHPG(D2) to treat HSV. It is also better than bromovinyldeoxy uridine(D16) being effective against both HSV 1 and HSV 2. As for the treatment of VZV the ACV's effectiveness has been controversial, in some case showed that ACV is less effective against CMV as compared with DHPG, Idoxuridine, Trifluridine, orAra-A. It is active against EBV, but only during the productive cycle. The combined clinical use of ACV and interferon in the treatment of CMV is known to be synergistic effective.

The bases commonly employed in ACV ointments are polyethylene glycol(PEG), modification aqueous cream and dimethylsulfoxide(DMSO). Corey, L. et al., reported in 1982 that the absorption of ACV through an HSV-infected skin was minimal after the treatment with a 5% ACV ointment containing PEG as the base, 4–6 times a day for 5–7 consecutive days and the plasma concentration of the drug was below 0.023 mg/L, barely detectable by the method (American J. of Medicine, 73:326–34). In 1986 Freeman, D. L. et al. (J. of Infections Diseases, 153:64–70) compared the flux of ACV from three topical preparations made with different vehicles and found that the one with PEG as the base gave the least flux, while the fluxes from the other two with modification aqueous cream and DMSO as the bases were 8 and 10 times higher, respectively. This demonstrates that the use of different vehicles does make a difference. Recently, Greg, E. et al. (J. Invest. Dermatol. 98:856–63,1992) found in a clinic study that the effect of ACV in the treatment of HSV 1 is actually better with oral administration than with local application. The drug concentration in the skin after local application is 2–3 times lower than after given orally. However, it is still considered safer to give the drug locally Since ACV cannot be effective unless it can penetrate the epidermis into deeper layers, it is highly desirable to find an efficient penetration enhancer for it's local application. The present invention is a formulation that contains such enhancer notably from Chinese medicine herbs and was found to significantly improve the transdermal delivery of a number of antiviral drugs.

A transdermal delivery system is a drug delivery system that releases it's drug slowly and continuously at a controlled rate to the skin upon application. Once released, the drug penetrates the epidermis and enters the microcirculation, which carries it to the target site for an effect. The advantages of such systems are the ease of use, being relatively safe, and affording the interruption of the medication by simply peeling off or removing from the skin whenever an overdosing is suspected. The total skin surface area of adult is about 2 m2, and micro-circulation constitutes about one third of the general circulation. In recent years, therefore, transdermal delivery of drugs has attracted wide attention as a better way of giving drugs. The design of transdermal delivery systems can usually be such that the side effects generally seen with the administration of conventional dosage forms are minimized.

The performance of the transdermal delivery system, however, is limited by: the physicochemical properties of the drug such as the partition coefficient, concentration, the size and the polarity of the molecule; the components of the system such as the bases with differing polarities, viscosity and strength as solvents; and the physiological as well as pathological conditions of the skin such as the "reservoir" function of the stratum corneum, surface lipids, moisture content, temperature, sites, injuries, cutaneous metabolism etc. Today, the most common problem facing us for the development of such system is the lack of safe and effective substances that can be used as the enhancer for various drugs to be given topically.

In recent years Chinese medicines have made a significant progress are gaining wider acceptation by the public. In 1975, for instance, the Department of Health in Japan agreed to include a total of 210 Chinese medicines in its national health insurance policy. A survey of the formulations that contain the Chinese medicines revealed that a total of 150 formulations have glycyrrhiza radix as it's component, amounting to a frequency of 71.4%. This was followed, in order by: zingiberis rhizoma (42.9%), paeoniae radix (32.9%), cinnamoni cortex et caulis (29.5%), zizyphi fructus (31.9%), and hoelen (35.2%). The Japanese pharmacopoeia 2nd ed. lists 93 formulations, in which glycyrrhiza radix is still the one that appears most frequently. An appearance of other Chinese medicines in similar order is also noticed.

The main constituents of these Chinese medicines are as follows: in glycyrrhizae radix have glycyrrhizin and 18-β-glycyrrhizin acid; in zingiberis rhizoma is α-pinene, cineole and β-myrcene; in Gleditsia sinensis Lam. Is gledinin, tannins, and gleditschia saponin; in zizyphi fructus is ursolic acid and oleanolic acid; in hoelen is eburicoic acid, dehydroeburicoic acid, 3 β-o-acetyltumulosic acid, 3 β-o- acetyldehydrotumulosic acid, and ergosterol; in paeoniae radix is paeoni-florigenone, tetraundecagalloyl-glucose, oxypaeoniflorin, albiflorin, benzoylpaeoniflorin, (+)-catechin, paeo-niflorin, and procyanidin β-1; in cinnamoni cortex et caulis is cinnzeylanol, anhydrocinnzeylanine, cinnamyl acetate, cinnzeylanine, cinnamaldehyde, anhydrocinnzeylanol, and cinncassiol A.

Some of these constituents which described as above, have some surface active or able to lower the surface tension of the skin, thus facilitating the penetration of the drug into the skin. In vitro studies have proved that the glycyrrhetinic acid, and glycyrrhizin are possess anti-inflammatory property, the former two being also effective against paw swelling.

In 1987, segal, R. et al. discovered (U.S. Pat. No. 4,678, 772) that a gel made of 2% glycyrrhizin, 0.1% benzoic acid, and 0.2% IDU can be effectively used orally for the treatment of HSV. In that same year they compared (J. Clinic Pharm, 12:1–7) the therapeutic effectiveness against HSV at the lip and the nose of two products: one is a gel containing 2% glycyrrhizin and IDU, the other a VIRUSON marketed ointment only containing 5% IDU. They fount that the gel not only shortened the healing process, but also reduced the pain. A year after, Touitou, E. et al. reported (Drug Design and Delivery, 3:267–72) that using nude mice's skin in a diffusion study in vitro at 34° C. and 25° C., they were able to show that the fluxes of IDU from the gel were 6 and 20 times higher as compared to the ointment at the respective temperatures, the gel and the ointment being the same ones as used in Segal's study.

For safety, we have screened those Chinese medicine that are largely inert by themselves to be successfully used as enhancers. The present invention comprises such enhancers incorporated, along with an antiviral drug, in topical dosage forms such as sprays, ointments, gels, suspensions, patches or solutions. Among the enhancers thus employed are: any single constituent of the following six herbs: glycyrrhizae radix, zingiberis rhizoma, hoelen, paeoniae radix, zizyphi fructus and cinnamoni cortex et caulis; and other constituent of Chinese medicine show in tab. 2 and tab. 3.

BRIEF DESCRIPTION OF THE DRAWINGS

Table 1: A list of Antiviral drugs

Table 2-1 through 2-4: Chinese medicine used as enhancers for drug absorption through the skin.

Table 3-1 through 3-2: Chinese medicine used as enhancers for drug absorption through the skin (continued)

FIG. 1: Structures of acyclovir and other antiviral agents.

Figure 2:
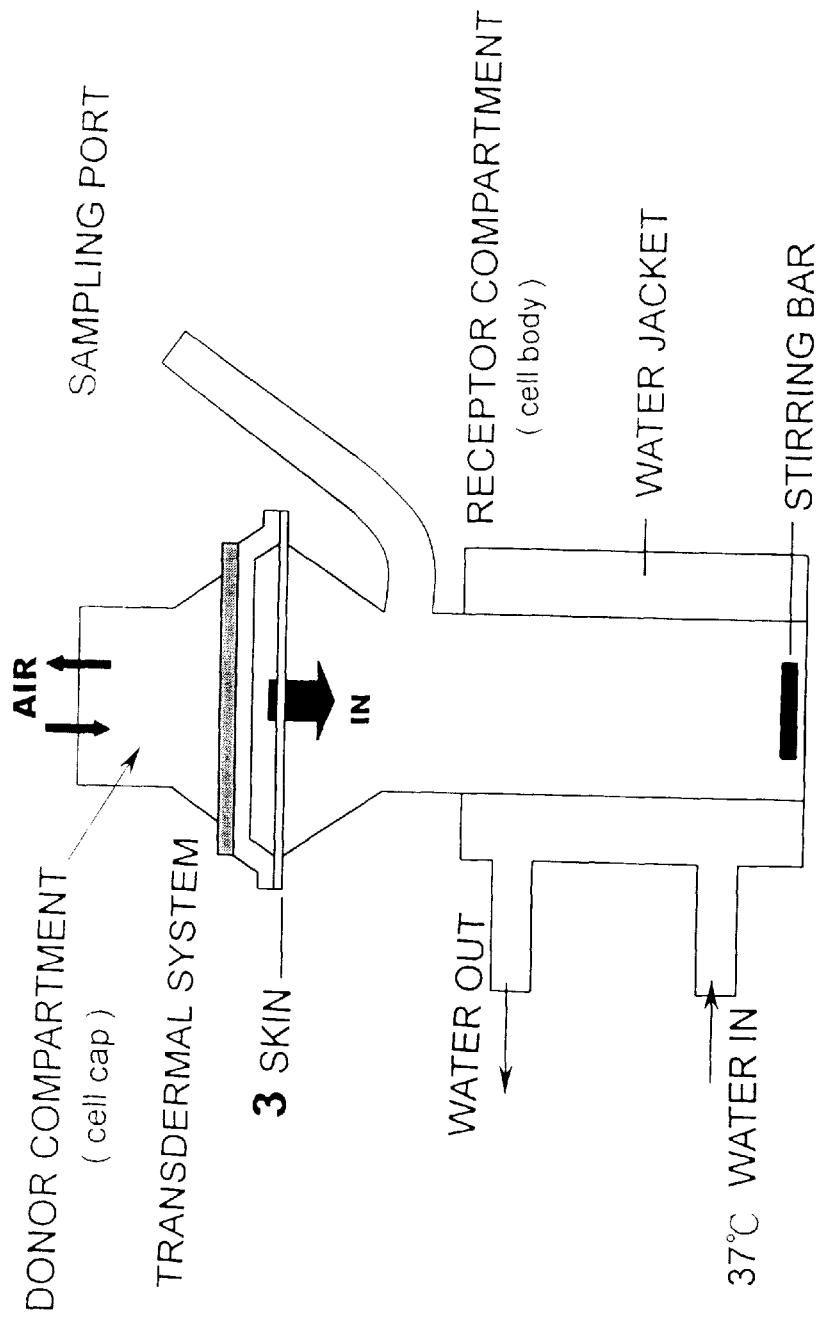

FIG. 2: Modified Franz diffusion cell.

Figure 3:
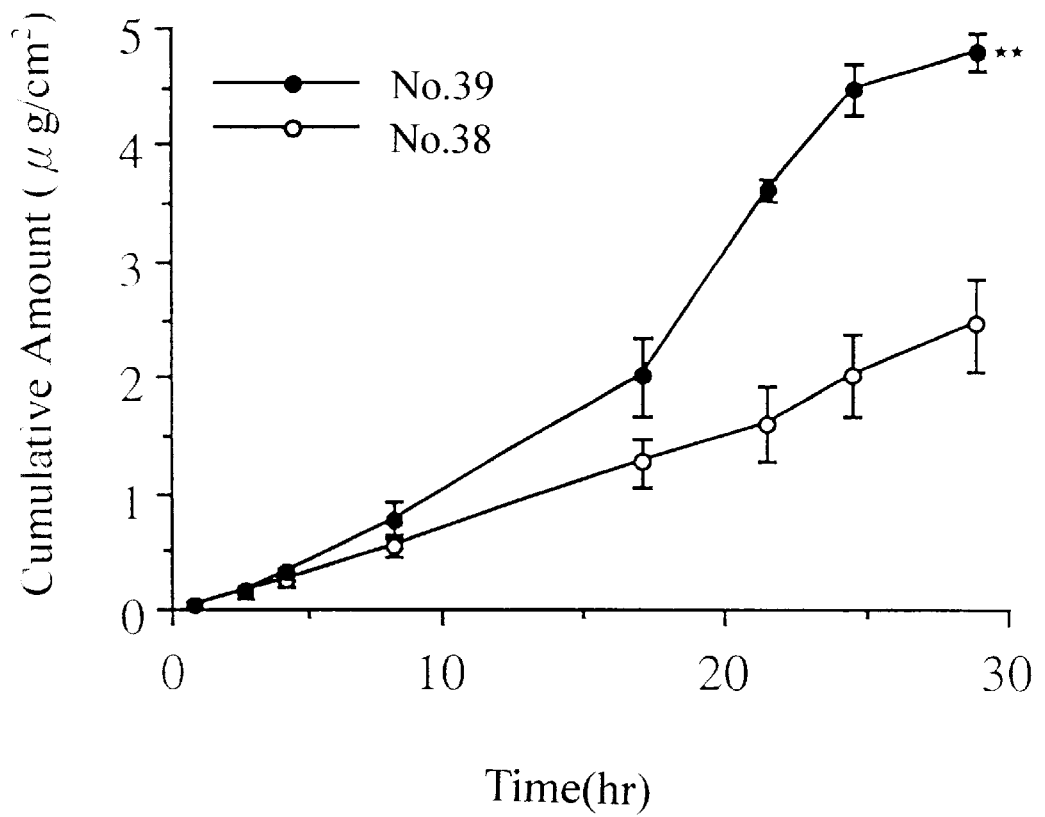

FIG. 3: In vitro "absorption" of ACV from the gels cmt'g CMC Na as the base as comganeel to the ointment cmt'g containing PES as the base.

Figure 4:
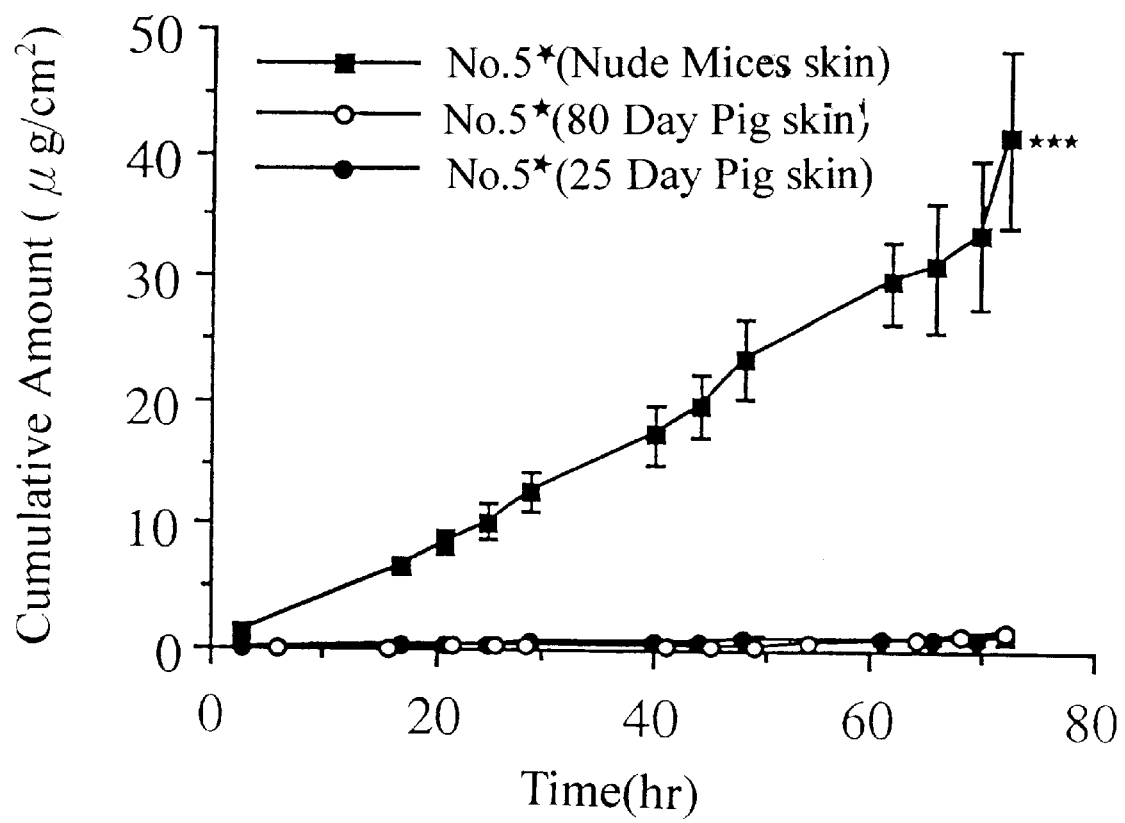

FIG. 4: Effect as CMC were on the in vitor "absorption" at ACV from gels cmt'g CMC Na as the base.

Figure 5:
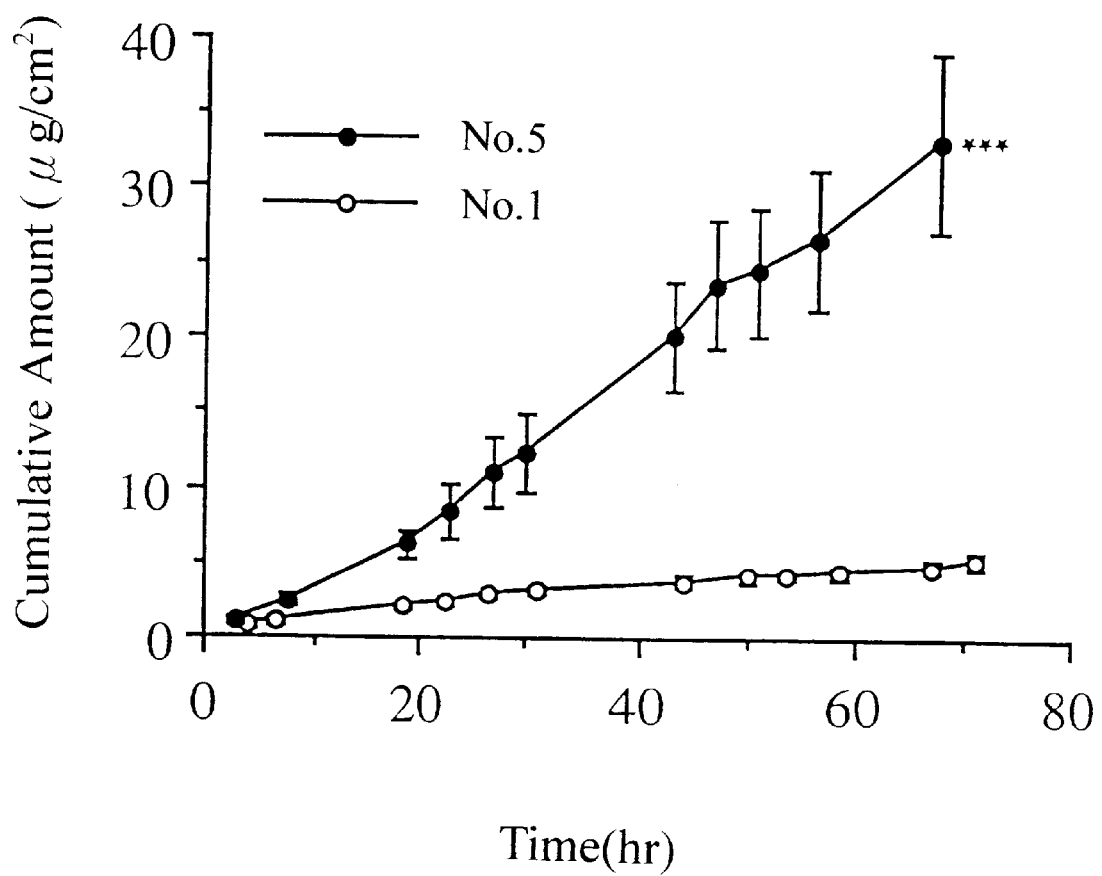

FIG. 5: Effect at enhancers on the in vitro "absorption" at ACV form gels cmt'g CMC Na as the base.

Figure 6:
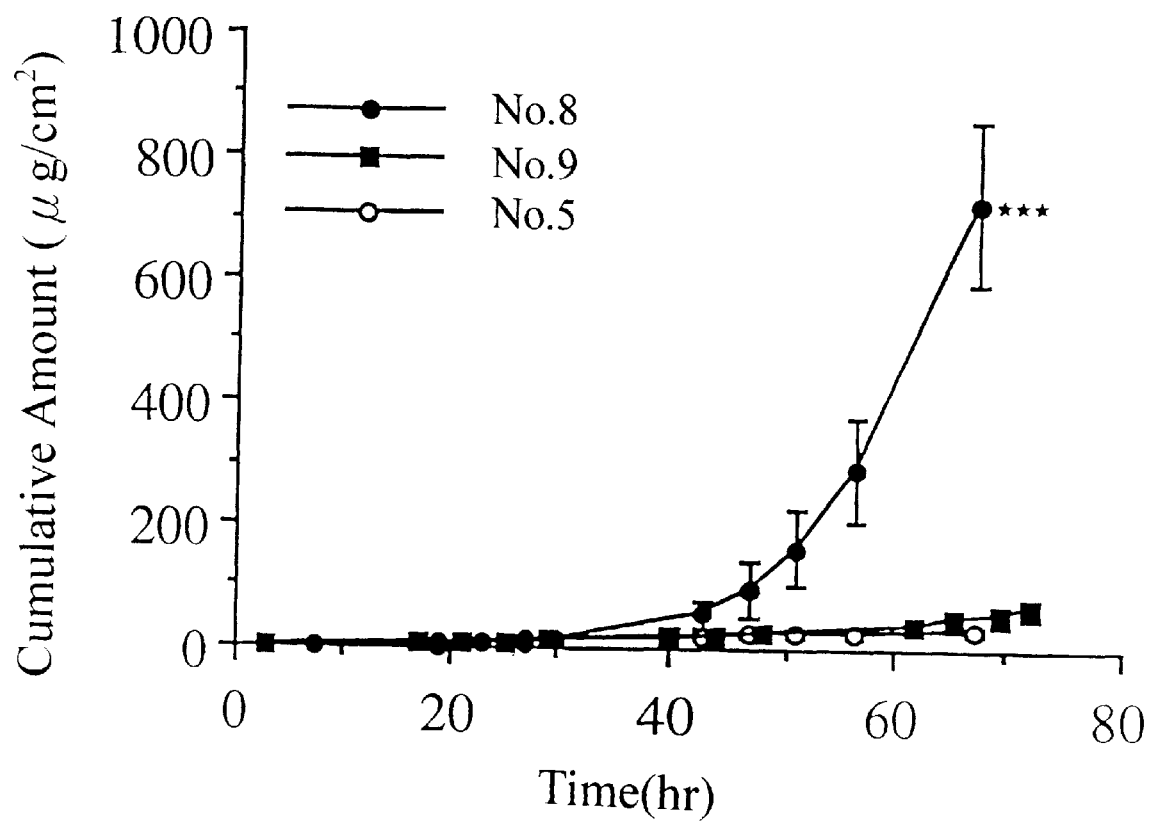

FIG. 6: Effect of the addition of a secondary enhancer on the in vitro "absorption" of ACV from gels cmt'g 2% GM.

Figure 7:
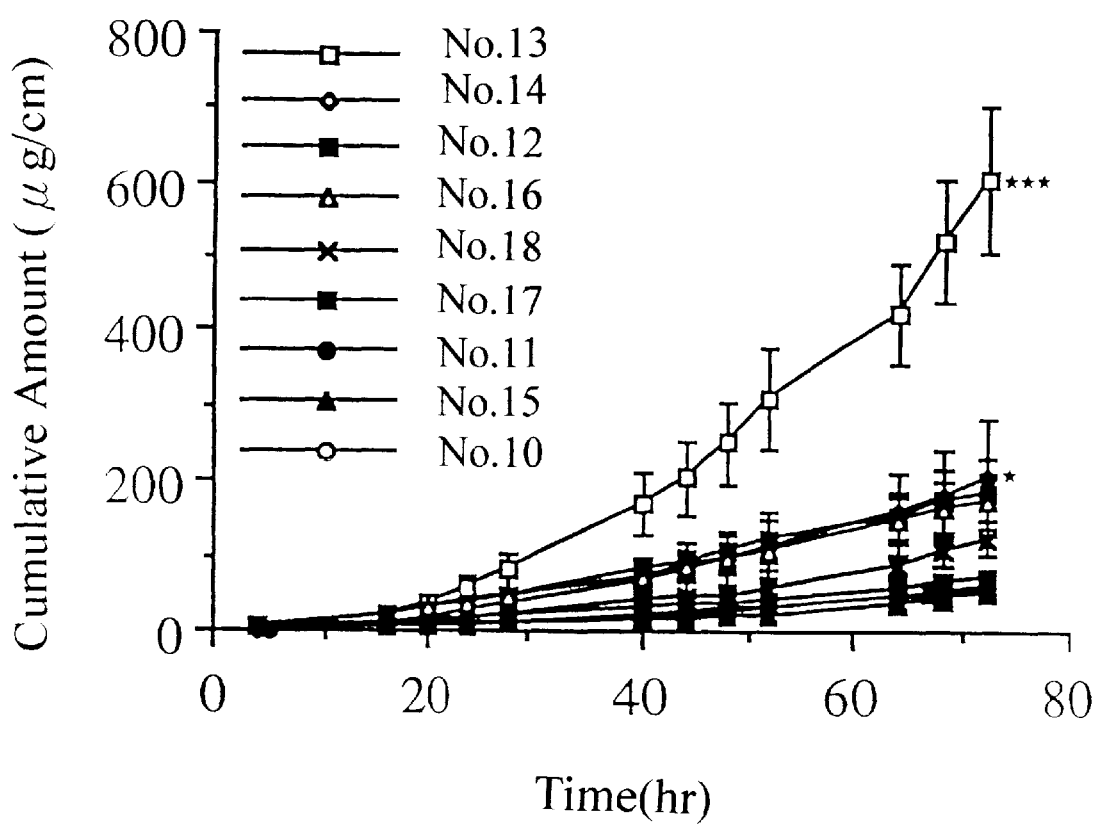

FIG. 7: Effect of Gleditsia sinensis Lam. extract as secondary enhancers in the in vitro "absorption" at ACV from gels cmt'g 2% GM.

Figure 8:
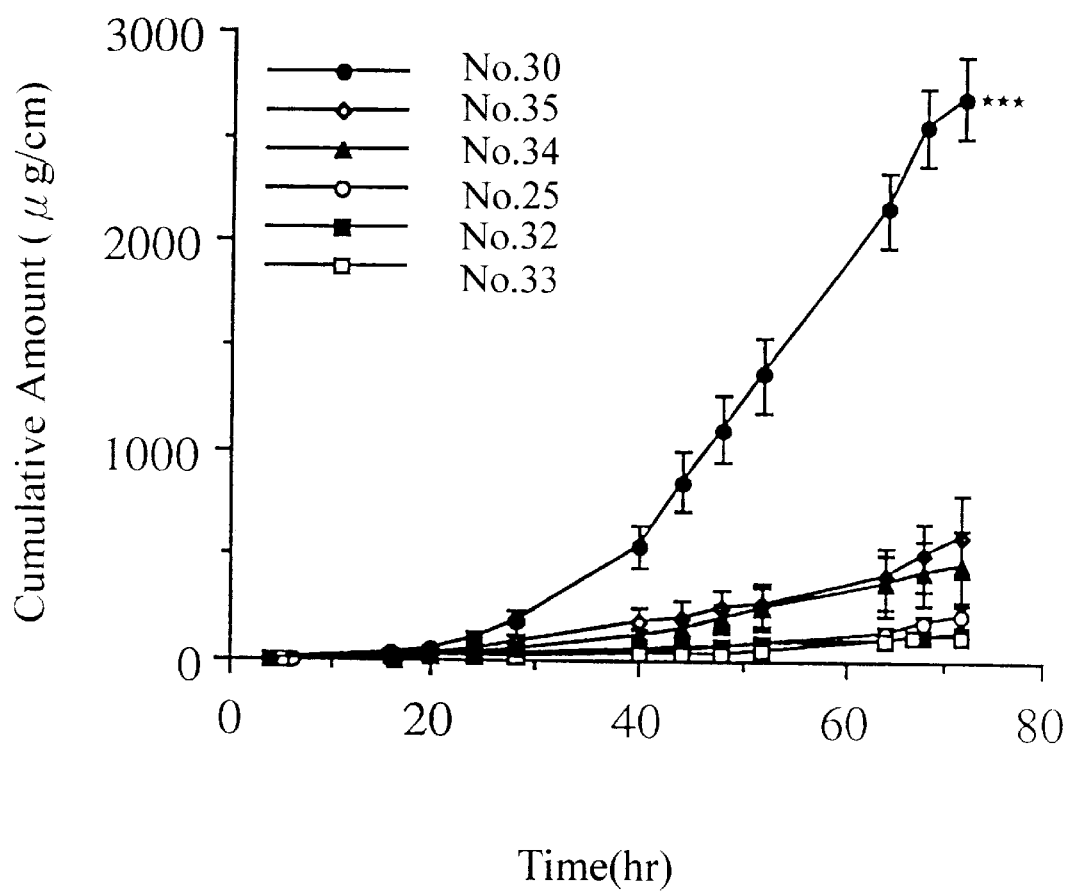

FIG. 8: Distribution of ACV in different skin layers after at applications of formulations for 72 hrs to a rabbit's ears, ( ) shows the congeel formulations.

Figure 9:
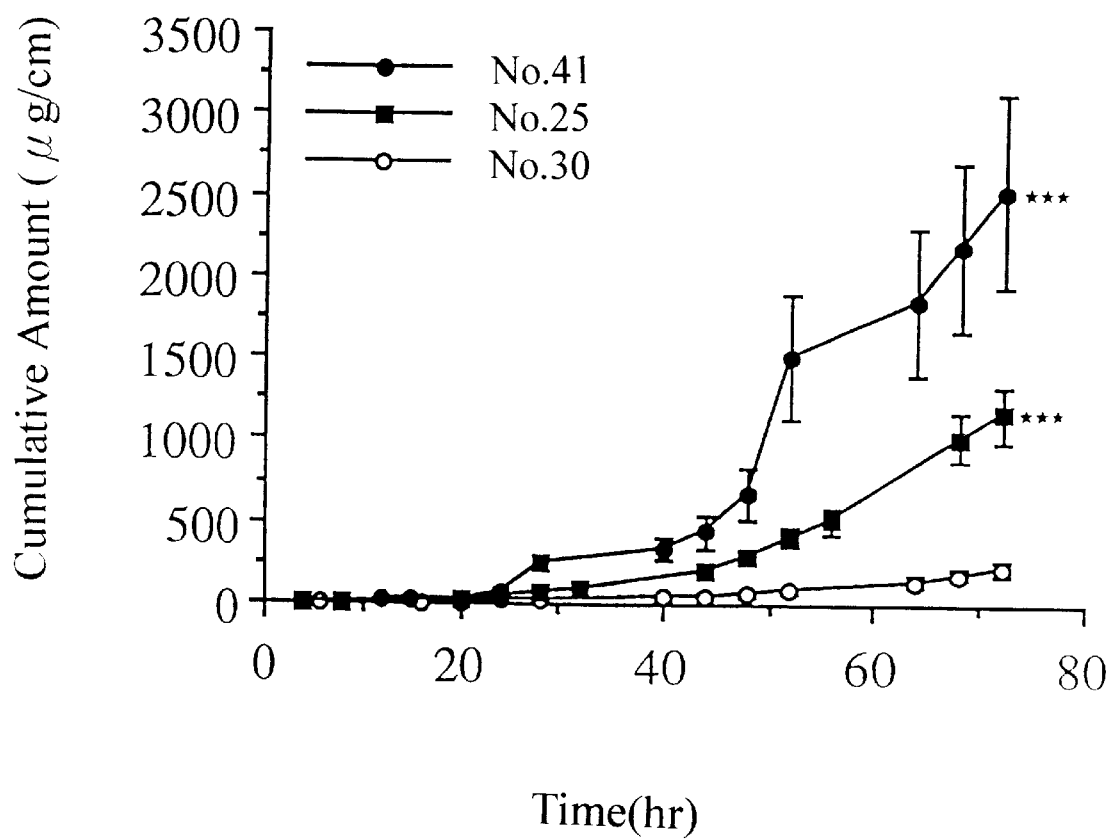

FIG. 9: Blood concentrations of ACV after applications him of 4 formulations to rabbits' ears; ( ) show the comgeel formulations.

Figure 10:
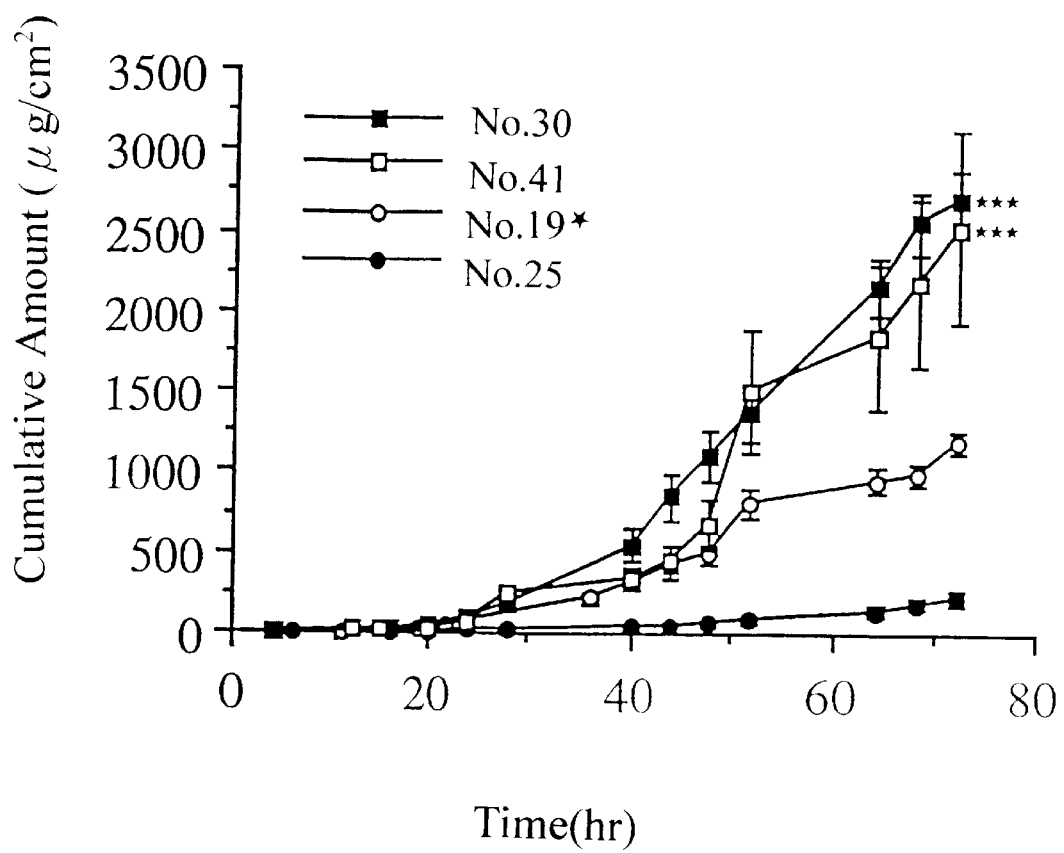

FIG. 10: Amount of acyclovir in the liver, heart, kindey, brain, lung, muscle and plasma of rabbits after applications of 4 acyclorir formulations on the ear for 72 hrs. The amount of acyclovir in the plasma and various tissues were compared using onewayANOVA . ($*P<0.05, P<0.01, *P<0.001$; ( ) shows the compared formulation.

Figure 11:
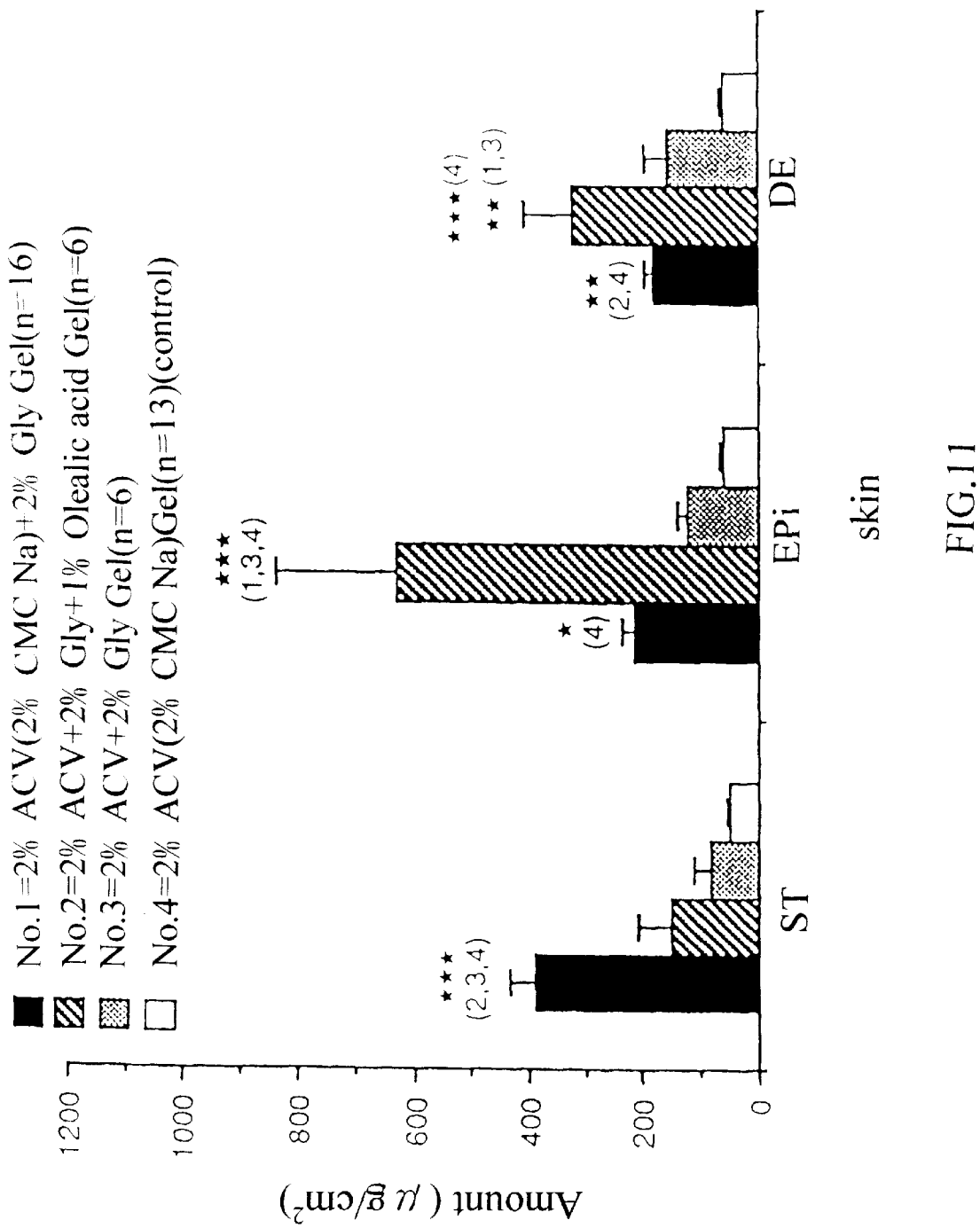

FIG. 11: human skin amount of ACV

Figure 12:
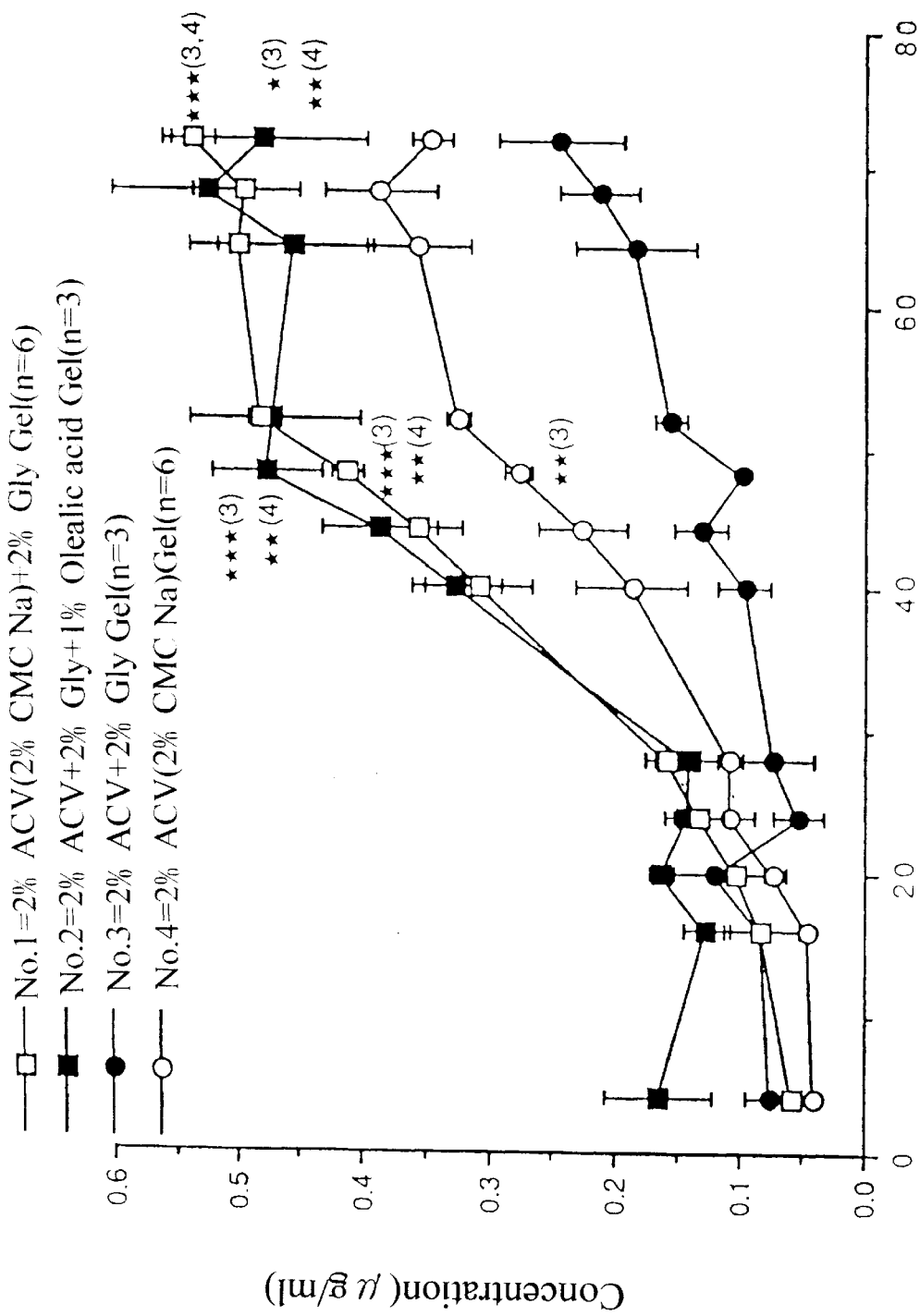

FIG. 12: Relationship betwiin lipophilic index (log K') Values of flycyrrhizin 18-β-glycyrrhetinic acid, β-myrcene, (IS)-(−)-α-pinene, and (+)-α-pinene and methanol concentration (V/V, %) in the mobile phase.

Figure 13:
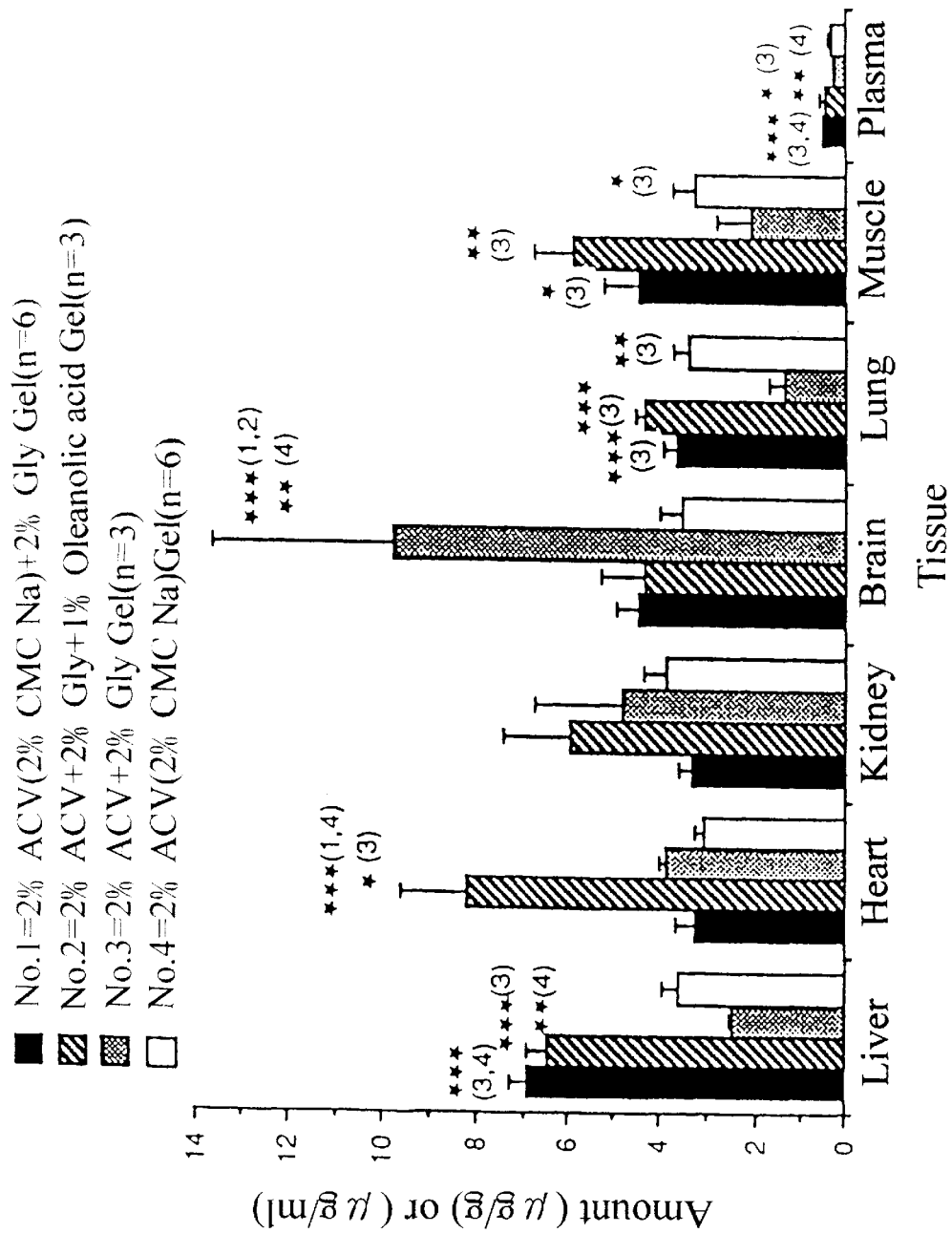

FIG. 13: In vitro "absorption" of aqueous from agreeous solutions cmt'g GM.

Figure 14:
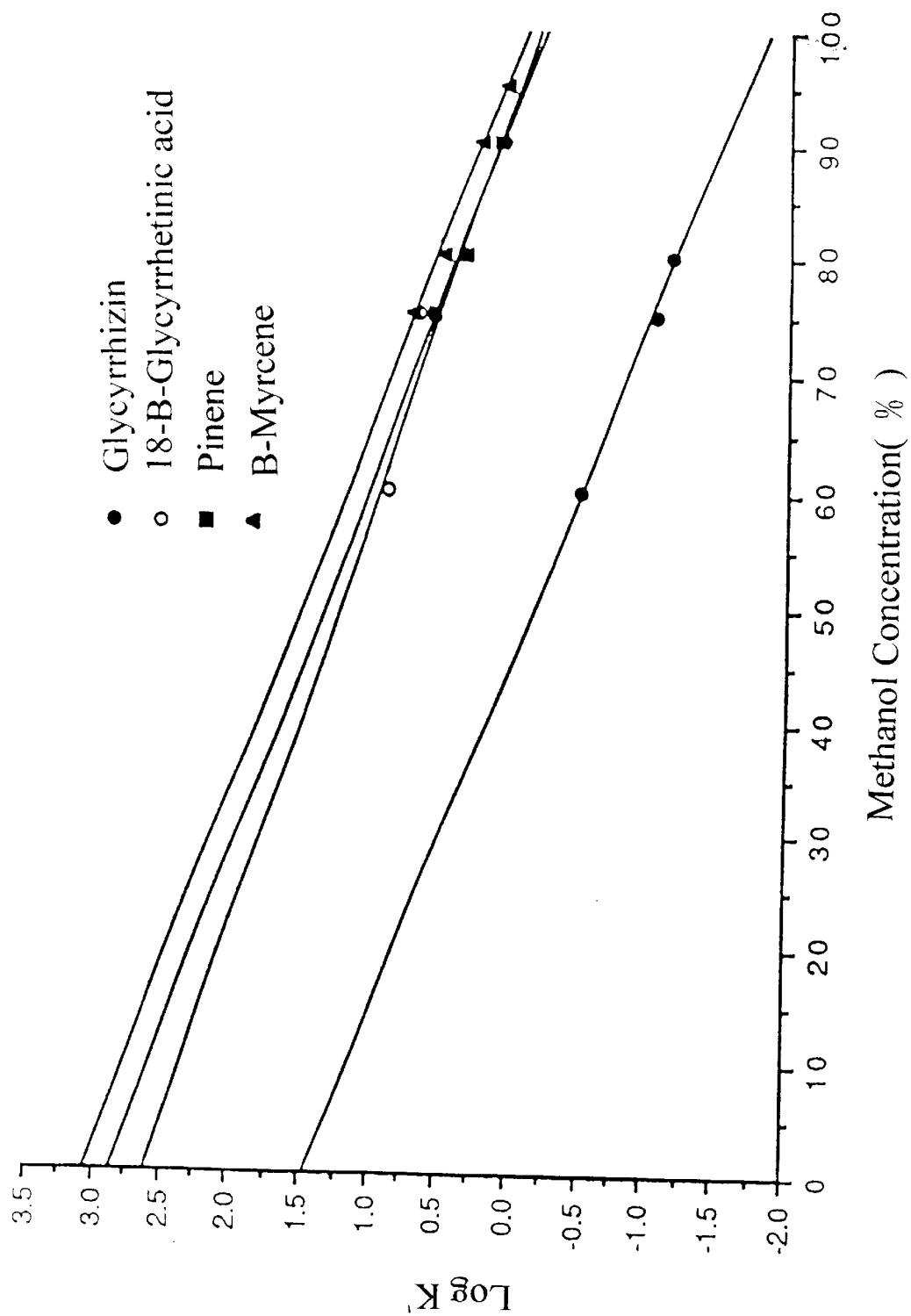

FIG. 14: In vitro "absorption" of ACV from gels through skins of different species.

BRIEF SUMMARY OF THE INVENTION

The antiviral drugs that are contained in the present invention include: ACV(D1) and other nucleoside analogs of structures shown in FIG. 1, with ACV, DHPG(D2), Desciclovir (D3), Vidarabine(Ara-A, D4), Carbovir(D5), DDA (D6), DDI (D7), Cordycepin(D8), Deoxyguanosine(D9), HPMPA(D10), Cytarabine (D11), DDC(12), Zidovudine (AZT, ZDV, D13), Deoxythymidine (D15), d4T(D14), IDC (D18), BVDU(D16), FIAC(D17), EDU(D19), F3T(D20), Ara-T(D21), HPMPC(D22), Ribavirin(D23), Riboxamide (D24), amantadine(D25), Rimantidine(D26), Tromantadine (D27), Arildone(D28), Enviroxime(D30), Foscamet sodium (D31), and Moroxydine(D29) . Among those antiviral drugs the ACV, DHPG(D2), Vidarabine(Ara-A, D4), BVDU (D16), FIAC(D17), F3T (D20) being the preferred ones.

The present invention comprises 0.1–30% of antiviral drugs as the main ingredient in conventional topical dosage forms such as ointments, suspensions, patches, sprays, solutions or gel. Specifically, for ACV(D1), DHPG(D2), Ara-A (D4), BVDU(D16), FIAC(D17) and F3T(D20) the most preferable concentration range is 0.1–10%. Irrespective of the dosage forms, the preferable amount of vehicle employed is 2–99.95%. The vehicles employed in the preparation of ointments are: 5% of ethyleneglycol(EG), 42.5–45% of PEG 400, and 42.5–45% of PEG 4000. Gels are classified into three types, which depends on the vehicles chosen: type 1 that contains 2–6% of carboxymethylcellulose sodium(CMC Na) and 50% of glycerin; type 2 that contains 20% of EG and 2% of CMC Na; and type 3 that contains 20% of EG only. All three types contain a suitable amount of water. Suspensions are made of 50–98% of EG and water. Solutions are made with sufficient amount of water with the aid of sonication. All formulations contain 0.05–20% of Chinese medicine enhancer, with 0.1–8% being most preferable.

The in vitro diffusion set-up employed in the development of the present invention is a modified Franz cell as shown in FIG. 2. It consists of two parts: the lower part is the receptor compartment and contains a solution of 0.15 N NaCl preserved with an antibiotic, the solution being stirred magnetically at 600 rpm; the upper part is the donor compartment and contains 0.25 or 0.5 g of the formulation, which is covered with a plastic sheet. In between these two parts is the skin obtained from either an animal source or human and these are held together by a clip. The lower part has a water jacket, through which water is circulated to maintain the temperature constant at 37° C. At specified times a 200 μl sample is withdrawn from the sampling port, which is immediately replaced by an equal amount of NaCl solution to keep a constant volume. To each sample, 200 µl of a solution containing 5 µg/ml of acetaminophen is added as the internal standard, and the drug content of each sample is analyzed by a HPLC method.

The loss of drug dues to metabolism or any unrelated causes during the 72 hr. experimental period is evaluated from the calculation of the % recovery according to the following equation:

$$R(\%) = \frac{A' \text{ total}}{A \text{ total}} \times 100\%$$

Where,

R: the recovery

A total: total amount of the drug before the experiment

A' total: total amount of the drug after the experiment

And

A' total=A' donor+A' skin+A' receptor

A total=A donor

Whereas

A' donor: the residual amount of drug remained in the donor compartment after the experiment A' skin: the residual amount of drug remained in the skin after the experiment A' receptor: the total amount of drug in the receptor compartment after the experiment A donor: the total amount of drug in the donor compartment before the experiment The skin specimen employed in the in vitro tests are obtained from human placenta, snakes, pigs, ICR (or Balb/c) nude mice and human skin. In vivo tests using rabbits are also conducted, in which case the formulation is applied onto the ear for 72 hours and the drug levels in different layers of skin and other tissues, including the liver, heart, kidney, brain, lung, muscle, and plasma are determined. From such tests we have discovered that a selection of the said substances from Chinese medicine have a significant enhance effect of promoting the absorption of antiviral drugs through the skin.

Marketed ACV ointments contain mostly PEG, modification aqueous cream, or DMSO as the base. We have found that gels made with 2% of CMC Na as the base are far better than the ointments made with PEG as the base. FIG. 3 compares the total "absorption" during 72 hrs. from two such preparations and gives that the total amount "absorbed" per unit area of the skin was 7 times higher with the gel formulation than with the ointment(34.9 μg/cm vs. 5.3 μg/cm ) . While a significant further increase in "absorption" was achieved when 2% of glycyrrhizin was added to the gel formulation. This is shown in FIG. 4. It is also noted that the enhancing effect of glycyrrhizin is apparently dose-dependent, at least in this case, as the "absorption" fell back to the control level when less than 2% of glycyrrhizin was added.

Based on such gel formulations that contain 2% of CMC Na, we have evaluated a number of the said substances as Chinese medicine enhancer. These include thus constituents as (1s)-(−)-α-pinene from the plants of cinae Flos, cyperi rhizoma valerianae radix, menthae herba, perillae herba, magnoliae flos, zizyphi fructus, piperis fructus, magnoliae cortex, croci stigma, zedoariae rhizoma, amomi cardamomi fructus, and zingiberis rhizoma; the ursolic acid from uvae ursi folium, corni fructus, zizyphi fructus; the 18-β-glycyrrhetinic acid and glycyrrhizin from glycyrrhizae radix; the oleanolic acid from corni fructus, forsythiae fructus, caryophylli flos, zizyphi fructus; the cineole from magnoliae flos, curcumae tuber, croci stigma; the α-(+)-pinene from foeniculi fructs, myristicae semen; β-myrcene from zingiberis rhizome, lupuli strobilus, amomi cardamomi fructus; the tannins and saponin from paeoniae radix, cinnamoni cortex et caulis, Gleditsia sinensis Lam., rhei rhizoma, alismatisrhizoma, corni fructus. euphorbiae kansui radix, tragacantha, persicae semen, cimicifugae rhizoma, mori radicis cortex.

The total cumulative amount of ACV "absorbed" per unit area of the skin during 72 hrs. from gels containing 8 different enhancers are compared with that of the control (Formula No.10) in FIG. 5. The beneficiary effect of the enhancer is obvious, especially that of glycyrrhizin (Formula NO. 13) and oleanolic acid (Formula No. 14), both resulting in an "absorption" of 605.3 μg/cm2 and 206.4 μg/cm$^2$ respectively. On the control (Formula NO.10) in FIG. 5 gave "absorption" of 53.4 μg/cm$^2$, recalling from FIG. 3 that the corresponding figure for the ointment (Formula NO.1) was only 5.3 μg/cm$^2$, the improvements are even greater. The addition of a second enhancer to the gel containing 2% of glycyrrhizin has both positive and negative effects depending on this second enhancer chosen. As shown in FIG. 8 a dramatic positive effect was seen in the case of 1% oleanolic acid (Formula NO. 30). It is also shown in the same figure that glycyrrhizin, when used alone is more effective in a suspension formulation (Formula NO.35) than in the gel formulation (Formula NO.25). The effect of inclusion of 1% extract from Gleditsia sinensis Lam. as the second enhancer (Formula NO. 41 in FIG. 7) is comparable to that of 1% oleanolic acid (Formula NO.30).

The distribution of ACV among different skin layers was examined in an in vivo test after a patch that contains the drug formulation was attached to a rabbit's ear for 72 hrs. FIG. 8 shows that the distribution varies somewhat with the stratum corneum, while those containing in combination glycyrrhizin(2%) and oleanolic acid(1%) favor the epidermis. The plasma concentration of the drug was also examined in the same test and was found to have noticeably increased when formulations containing either 2% of glycyrrhizin or a combination of 2% of glycyrrhizin and 1% of oleanolic acid were used (FIG. 9), producing a concentration in the respective case of 0.53±0.02 μg/ml and 0.48±0.03 μg/ml at 72 hrs. This compares favorably to the control figure of 0.35±0.03 μg/ml. Increased distributions of the drug in heart, liver, kidney, brain, lung, muscle, and plasma at 72 hrs. were also observed (FIG. 10), but the amounts increased in these organs were relatively small and considered harmless. As shown in FIG. 11 the 6 times human skin concentration of 2% glycyrrhizin than control.

Since drugs are said to pass the skin through either polar pathways or norpolar pathways, it is instructive to examine the solubility parameters and lipophilic indices of such enhancers, the latter being calculated from the defermination of their k' values in the mobile phase of varying methanol concentrations of the HPLC method used. As shown in FIG. 12 and Tab.4 glycyrrhizin and oleanolic acid exhibit opposite polarities, with glycyrrhizin being more polar and favoring a polar pathway. A combination of glycyrrhizin and oleanolic acid, therefore conceivably helps the passage of ACV through the skin via both pathways, which may account for its superior behavoir in promoting the absorption.

It is well known that ACV by itself is difficult to penetrate into the skin. However, the locus of diseases requiring ACV treatment resides mostly in the base epidermis, between epidermis and dermis, the inner layer of the skin. Most marketed ACV ointments are made with PEG, modification aqueous cream or DMSO as the base and are found less effective. The present invention embodies the largely inert substances from Chinese medicine such as cinae Flos, cyperi rhizoma, valerianae radix, menthae herba, perillae herba, magnoliae flos, zizyphi fructus, piperis fructus, magnoliae cortex, croci stigma, zedoariae rhizoma, amomi cardamomi fructus, zingiberis rhizoma; uvae ursi folium, corni fructus, zizyphi fructus, glycyrrhizae radix, corni fructus, agnoliae flos, forsythiae fructus, caryophylli flos, zizyphi fructus, curcumae tuber, croci stigma, foeniculi fructs, myristicae semen, zingiberis rhizome,lupuli strobilus, amomi cardamomi fructus,paeoniae radix, cinnamoni cortex et caulis,rhei rhizoma, Gleditsia sinensis Lam., alismatis rhizoma, corni fructus, euphorbiae kansui radix, tragacantha, persicae semen, cimicifugae rhizoma, morn radicis cortex etc. as the Chinese medicine enhancers to promote transdermal absorptions. Tests, as described above have verified that the absorption of ACV through the skin from the present invention is nearly 500 times higher than that from the conventional ointment products containing no such enhancers.

Concerning the factor of transdermal capabilities of skin specimen and dosage, in vitro tests are obtained from the human placenta, snakes, pigs and ICR (or Balb/c) nude mice were used. For example, as shown in FIG. 13, the accumulated total amount of ACV that penetrated the snake skin during 28.75 hrs, from an aqueous solution containing 0.01% of ACV and 0.01% glycyrrhizin (Formula NO.39) was found to be 4.8 $\mu g/cm^2$, which is twice as much as that observed with the control formulation (No. 38) containing no glycyrrhizin. We have also found that the in vitro "aborption" of ACV was much greater with nude mice skin than with either 80-day or 25-day old pig skin from a gel containing 2% of ACV and 2% of CMC Na. This is shown in FIG. 14.

Antiviral drugs other than ACV that are being used locally include: vidavabine(D4), trifluidine(D20) and IDU(D18). These drugs having relatively low toxicities are suitable candidates to be used in the present invention too. As noted above a combination of several enhancers, instead of a single one, can be used more beneficially in the formulations.

The following examples are presented as an illustration and not to be constructed as limiting of the claims in any way. Unless otherwise stated all percentages in the following examples are by weight.

EXAMPLE 1

Preparation of Acyclovir Ointment

Dissolve 5% of acyclovir in 5% of EG preheated to 75° C. In a separate container mix 45% of PEG400 and 45% of PEG4000, and heat to 75° C. Mix the two solutions, and cool rapidly at 25° C. with stirring.

EXAMPLE 2–5

Preparation of ACV Ointment Containing Enhancers

Add 1% of Gleditsia sinensis Lam. extract or 1%, 2%, 5% of glycyrrhezin to the EG solution in example 1, and follow the same procedure.

EXAMPLE 6–8

Preparation of the Type I Acyclovir Gel

Dissolve 2% of ACV and 2% or 4%, 6% of CMC Na in sufficient amount of water, and mix with 50% of glycerin. Add sufficient amount of water to 20 ml.

EXAMPLE 9–10

Preparation of type I ACV gel containing Glycyrrhizin

Dissolve 2% or 5% of glycyrrhizin along with 2% of CMC Na in sufficient amount of water, and follow the procedure given in example 6.

EXAMPLE 11

Preparation of Type II Acyclovir Gel

Dissolve 2% of ACV in 20% of EG. In a separate container dissolve 2% of CMC Na in sufficient amount of water. Mix the two solutions and add sufficient amount of water to 20 ml.

EXAMPLE 12–19

Preparation of Type II ACV Gel Containing Enhancers

Following the procedure given in Example 11, dissolve in the EG solution the following, separately: 2% of ursolic acid, 2% of glycyrrhizin, 2% of 18-β-glycyrrhetinic acid, 2% of oleanolic acid, 5% of β-myrcene, 5% of (+)-α-pinene and 5% of cineole, 5% of (1s)-(–)-α-pinene.

EXAMPLE 20

Preparation of the Type III Acyclovir Gel Containing Glycyrrhizin

Dissolve 0.247% of acyclovir in 5% of EG and add 2% of glycyrrhizin. Mix in a mortar with a suitable amount of water. Centrifuge the mixture at 3,000 rpm for 30 minutes and separate the supernatant.

EXAMPLE 21

Preparation of the Type III Acyclovir Gel Containing Glycyrrhizin

Following the procedure given in Example 20, prepare the gel containing 0.653% of ACV and 1% of glycyrrhizin instead.

EXAMPLE 22

Preparation of the Type III Acyclovir Gel Containing Glycyrrhizin

Following the procedure given in Example 20, prepare the gel containing 0.852% of ACV and 3% of glycyrrhizin instead.

EXAMPLE 23

Preparation of the Type III ACV Gel Containing Glycyrrhizin and Oleanolic Acid

Following the procedure given in Ex. 20, prepare the gel containing 0.305% of acyclovir instead and 5% of oleic acid additionally.

EXAMPLE 24

Preparation of Type III Acyclovir Gel Containing Glycyrrhizin and 18-β-Glycyrrhetinic Acid Following the procedure given in Example 20, prepare the gel containing 0.648% of acyclovir instead and 2% of 18-β-glycyrrhetinic acid additionally.

EXAMPLE 25

Preparation of Type III ACV Gel Containing Glycyrrhizin

Following the procedure given in Example 20, prepare the gel containing 1% of ACV instead.

EXAMPLE 26–32

Preparation of Type III Acyclovir Gel Containing Chinese Medicine Enhancers

Following the procedure given in Example 25, dissolve in the gel the following additional Chinese medicine enhancers separately: 20% of dimethylsulfoid, 5% of (+)-α-pinene, 1% of ursolic acid, 1% and 2% of oleanolic acid, and 1% and 2% of extracted Gleditsia sinensis Lam.

EXAMPLE 33

Preparation of Acyclovir Suspensions

Mix 2% of acyclovir in 98% of ethylene glycol in a mortar.

EXAMPLE 34

Preparation of Acyclovir Suspensions Containing Glycyrrhizin

Following the procedure given in Example 33, prepare the suspension containing 50% of ethylene glycol (EG) instead and 2% of glycyrrhizin in addition.

EXAMPLE 35

Preparation of Acyclovir Suspensions Containing 18-β-Glycyrrhetinic Acid

Following the procedure given in Example 33, prepare the suspension containing 96% of EG instead and 2% of 18-β-glycyrrhetinic acid.

EXAMPLE 36

Preparation of Acyclovir Suspension Containing Gleditsia Sinensis Lam

Following the procedure given in Example 33, prepare the suspension containing 5% of acyclovir, 94% of EG instead and 1% of Gleditsia sinensis Lam. in addition.

EXAMPLE 37

Preparation of Acyclovir Solution

Dissolve 0.1% of ACV in water with the aid of sonication.

EXAMPLE 38

Preparation of Acyclovir Solution Containing Glycyrrhizin

Following the procedure given in Example 37, prepare the solution containing additionally 0.1% of glycyrrhizin.

EXAMPLE 39

Preparation of Acyclovir Solution

Following the procedure given in Example 37, prepare the solution containing instead 0.05% of acyclovir.

EXAMPLE 40

Preparation of Acyclovir Solution Containing Gleditsia Sinensis Lam

Following the procedure given in Example 39, prepare the solution containing in addition 0.005% of Gleditsia sinensis Lam. extract.

EXAMPLE 41

Preparation of Antiviral Agent Transdermal Delivery System

Following the procedure given in Example 1–37, prepare such products, which contain Ara-A or trifluridine instead of ACV as the antiviral agent.

EXAMPLE 42

Preparation of Antiviral Agent Transdermal Delivery System

Following the procedure given in Example 1–37, prepare such products, which contain glycyrrhizae radix, hoelen, cinnamoni cortex et caulis, atractylodis rhizoma, citri exocarpium, amomi semen, angelicae sinensis radix, ligustici rhizoma, citri fructus, artemisiae capillaris herba, caryophylli flos, chrysanthemum, saussursae radix, sengae radix, schizonepetae herba, foeniculi fructus, eucalypti folium, evodiae fructus, zanthoxyli fructus, asari herba cum radice, houttuyniae herba, schizandrae fructus, alpiniae fructus, alismatis rhizoma, mori radicis cortex, euphorbiae kansui radix, tragacantha, persicae semen, cimicifugae rhizoma, paeoniae radix, and rhei rhizoma instead of glycyrrhizin, 18-β-glycyrrhetinic acid, (+)-α-pinene, oleanolic acid, Gleditsia sienensis Lam., and ursolic acid as the enhancer.

EXAMPLE 43

In Vitro Test

The total amount "absorbed" of acyclovir through the skin in 72 hours from preparations containing enhanceress was determined in vitro as described using human plancenta, snake, 25- and 80-day old pigs, 7 to 9-week old ICR or Balb/c female nude mice and human as skin specimens. Samples were analysed by a HPLC method. Corrections were made as described if needed.

EXAMPLE 44

In Vivo Test

The in vivo absorption and distribution of acyclovir from preparations containing enhanceress, were evaluation from the determinations of its concentration in different layers of skin, blood and various tissues after the preparations were applied to rabbits' ears for 72 hrs.

TABLE 1

NOMENCLATURE OF THE ANTIVIRAL DRUGS

| No. | Drug name | Chemical names | Common trade names | Common abbreviation |
|---|---|---|---|---|
| D1 | Acyclovir | 9-[(2-Hydroxyethoxy)methyl]-guanine; 2-amino-1,9-dihydro-9-[2-hydroxyethoxy]6H-purin-6-one; acycloguanosine | Zovirax | ACV |
| D2 | Ganciclovir | 9-(1,3-Dihydroxy-2-propoxy-methyl)guanine; 2-amino-1,9-dihydro-9-(1,3)-dihydroxy-2-propoxymethyl)6H-purin-6-one | | DHPG |
| D3 | Descielovir | 2-[(2-Amino-9H-purin-9-yl)-methoxy]ethanol deoxyacyclovir | | DCV |
| D4 | Vidarabine | 9-beta-D-arabinofuranosyl-9H-purine-6-amine; 9-beta-D-arabinofuranosyladenine; adenine arabinoside | Vira-A | Ara-A |
| D5 | Carbovir | Carbocyclic 2',3'-didehydro-2',3'-dideoxyguanosine | | |
| D6 | 2',3'-Dideoxyinosine | 2',3'-Dideoxy-9-beta-ribofuranosyl-9H-purina-6-amine | | DDA |
| D7 | 2',3'-Dideoxyinosine | 2',3'-Dideoxy-9-beta-ribofuranosyl-1,9-dihydro-6H-purin-6-one | | DDI |
| D8 | Cordyceptin | 3'-Deoxyadenosine; 9-cordyceposidoadenine | | |
| D9 | Deoxyguanosine | | | |
| D10 | [9-(3-Hydroxy-2-phosphonylmethoxylpropyl)adenosine] | [9-(3-Hydroxy-2-phosphonylmethoxypropyl)adenosine] | | HPMPA |
| D11 | Cytarabine | 4-Amino-1-beta-D-arabinofuranosyl-2(1H)-pyrimidinone; 1-beta-D-arabinofuranosylcytosine, 1-beta-cytosine arabinoside | Alexan; Arabitin; Aracytine; Ara-C; Aracytidine et al. | Ara-C |
| D12 | 2',3'-Dideoxycytidine | 2',3'-Dideoxy-4-amino-1-beta-D-ribofuranosyl]-2-(1H)-pyrimidinone | | DDC |
| D13 | Zidovudine | 1-(3-Azido-2,3-dideoxy-beta-D-erythro-pentofuranosyl) thymine; 3'-azido-3'-deoxythymidine | | ZDV, AZT |
| D14 | 2',3'-Didehydro-2',3'-deoxythymidine | 1-(2,3-didehydro-3-deoxy-beta-D-erythro-pentofuranosyl)thymine | | d4T |
| D15 | Deoxythymidine | | | |
| D16 | Bromovinyldeoxyuridine | 5-(2-Bromovinyl)-2'-deoxyuridine | | BVDU |
| D17 | 2'-Fluoro-5-iodoaracytosine | 2'-Fluoro-5-iodo-4-amino-1-beta-D-arabinofuranosyl-2(1H)-pyrimidinone; 2'-fluoro-5-iodo-1-beta-arabinofuranosylcytosine | | FIAC |
| D18 | 5-Iodo-2'-deoxycytidine | 2'-Deoxy-5-iodo-4-amino-1-beta-D-ribofuranosyl]-2-(1H)-pyrimidinone | | IDC |
| D19 | Deoxyuridine | 2'-Deoxyuridine; 1-(2-deoxy-beta-D-erythro-pentofuranosyl)uracil; 1-(2-deoxy-beta-D-ribofuranosyl)uracil; uracil deoxyriboside | | EDU |
| D20 | 5-Trifluoromethyl-2'-deoxyuridine | | | F3T |
| D21 | 1-beta-D-Arabinofuranosylthymine | | | Ara-T |
| D22 | [9-(3-Hydroxy-2-phosphonylmethoxy-propyl)cytidine] | [(9-(3-Hydroxy-2-phosphonylmethoxypropyl)cytidine] | | HPMPC |
| D23 | Ribavirin | 1-beta-D-Ribofuranosyl-1H-1,2,4-triazole-3-carboxamide | Viramid et al | RTCA |
| D24 | Riboxamide | 2-beta-D-Ribofuranosyl-4-thiazolcaboxamide; tiazofurin | | TCAR |
| D25 | Amantidine | Tricyclo[3.3.1.1]decan-1-amine; 1-adamantanamine; 1-aminoadamantane | Amazolon; Mantadix et al. | |
| D26 | Rimantidine | x-Methyltricyclo[3.3.1.1]decan-1-methanamine: x-methyl-1-adamantanmethylamine | Meraden | |
| D27 | Tromantadine | N-1-Adamantyl-N-[2-(dimethylamino)ethoxy]acetamide | | |
| D28 | Arildone | 4-[6-(2-Chloro-4-methoxyphenoxy)hexyl]3,5-heptanedione | | |
| D29 | Moroxydine | N-(Aminoiminomethyl)-4-morpholinecarboximid-amide; abitylguanide | Bioxine; Vironil; Virusmin et al. | ABOB |
| D30 | Enviroxime | 6-[(Hydroxyimino)phenylmethyl]-1-[(1-methylethyl)sulfonyl](1H)-benzimidazol-2-amine | | |
| D31 | Foscarnet sodium | Dihydroxyphosphinecarboxylic acid oxide trisodium salt; trisodium phosphonoformate | | |

Tab. 2-1

Glycyrrhizae Radix
  Glycyrrhizin, glycyrrhetinic acid, 18-β-glycyrrhetinic acid
Zingiberis Rhizoma
  α-Pinene, β-Myrcene, Cineole
Zizyphi Fructus
  Oleanolic acid, Ursolic acid, Betulonic acid, maslinic acid
    Zizyphus saponin I, Zizyphus saponin II, Zizyphus saponin III, Jujuboside B,
Gleditsia sinensis Lam.
  Gledinin, Gleditschia Saponin, Cetylalcohol, Nonacosane, Stigmasterol, Sitosterol
Hoelen
  Dehydroeburicoic acid, 3 β-O-acetyltumulosic acid, Eburicoic acid,3 β-O-acetyldehydro tumulosic acid, Ergosterol,
paeoniae radix
  Albiflorin, Paeoniflorin, Oxypaeconiflorin, Paeoniflorigenone, Benzoylpaeoniflorin, Tetraundeca, galloylglucose, (+)-Catechin, Procyanidin B-1
Cinnamoni Cortex et caulis
  Cinnamaldehyde, Cinnamyl acetate, Phenylpropyl acetate, Cinnzeylanol, Cinncassiol C3, Cinnzeylanine, Anhydrocinnzeylanine, Cinncassiol A 19-monoacetate, Cinncassiol D1, Cinncassiol E, Cinncassiol A 19-O- glucoside, Cinncassiol B 19-O-glucoside, Cinncassiol A, Procyanidin C1, Cinncassiol D2 19-O-glucoside Cinncassiol D3, Cinncassiol D1 19-O-glucoside, Cinncassiol D2, Cinncassiol C1, Cinncassiol C1 19-O-glucoside, Cinncassiol B, Gallic acid, Anhydrocinnzeylanol, Cinncassiol D4, Cinncassiol C2, Apigenin 3,7-dirhamnoside, Procyanidin B-2, Prolocatechuic acid, (−)-Epicatechin, Procyanidin B-5, Tab. 2-2

Cardamomi Fructus
  (+)-α-Terpinyl acetate, 1,8-Cineole, Sabinene Limionene, (+)-α-Terpineol Atractylodis Rhizoma
  Atractylon, Eudesma-414, Atractylencolide I, 7(11)-Dien-8-one Hinesol, Atractylenolide II, Atractylenolide III, Elemol, 3β-acetoxyatractylon, 3β-hydroxyatractylon, β-eudesmol, Atractylodine, Atractylodinol, acetylatractylodinol, Angelicae Sinensis radix
  Butylidenephthalide, $\Delta^{2,4}$-dihydrophthalic anhydride, n-Valerophenone-O-carboxylic acid Ginseng Radix
  Heptaedeca-1-en 4, 6-Dihn-3,9-diol panaxydol, 20-glucoginsenoside-Rf, Choline, β-Sitosterol glucoside, Ginsenoside-Rx(x-o, a1, a2, b1, b2, b3, (c, d, e, f, g1, g2, h1) Nicotinic acid, β-Sitosterol, β-Elemene, Panaxynol, Citri Exocarpium
  d-limonene, Linalool, Citral, Hesperidin, Citric acid,(−)-Synephrine, Neohesperidin, Naringin, Poncirin, Umbelliferone, Auraptene, Citroptene, Imperatorin, Isoimperatorin, Isoponcimarine, Scutellariae Radix
  Baicalin, Stigmasterol, Wogoin glucuronide, Wogonin, Baicalein, Oroxylin A, Oroxylin A glucuronide, 5,8-Dihydroxy-6,7-dimethoxy-flavone, Skullcap-Flavon I, 5,7,4'-Trihydroxy-8-methoxy flavone, Skullcap-Flavon II, 5,7,2',6'-Tetrahydroxy flavone, Campesterol, β-Sitosterol, Koganebananin Bupleuri Radix
  Saikosaponin a, c, d, Oleic adid, α-Spinasterol, $\Delta^7$ Stigmasterol, Linolenic acid, Lignoceric acid, Adonitol, Saikogenin F,E,C, Longispinogenin lignoceric acid, Palmitic acid, Angelicin, Stearic acid Tab. 2-3

Ligustici Rhizoma
  Cnidiuim lactone, Ferulic acid, Cnidilide, Neocnidilide

Rehmanniae Radix et rhizoma
  Rehmannoside A,B, Aucubin, Nelittoside, Rehmannioside, Lenuoride, Catalpol Pinelliae Tuber
  Homogentisic acid glucoside, 3,4-Dihydroxybenzaldehyde, Homnogentisic acid, 3,4-Dihydroxybenzaldehyde diglucoside, β-Sitosterolglucoside, Ephedrine, Choline, β-Sitosterol Rhei Rhizoma
  Chrysophanol, Aloe-emodin, Physcion, Emodin, Chrysophanol 1-glucoside Chrysophanol 8-glucoside, Rhein, (+)-Catechin, (−)-Epicatechin, Procyanidin B-1 3-O-gallate, Aloe-emodin-8-glucoside, Citreorosein, Physcion-8-glucoside, Emodin-1-glucoside Emodin-8-glucoside, Rhein-8-glucoside, Rhein-8-6-oxal-ylglucoside, Sennoside A, B, C, D, E, F, (−)-Epicatechin-3-O-gallate, Magnoliae Cortex
  β-Eudesmol, α-Pinene, β-Pinene, Camphene, Bornylacetate, Caryophylleneepoxide, Cryptomeridiol, Limonene, Magnolol, Honokiol, Magnocurarine, Magnoflorine, Anonaine, Liriodenine, Salicifoline, α-Eudesmol, Michelarbine Citri Fructus
  d-limonene, Linalool, Citral, Hesperidin, Citric acid, (−)-Synephrine, Neohesperidin, Naringin, Poncirin, Umbelliferone, Auraptene, Citroptene, Imperatorin, Isoimperatorin, Isoponcimarine, Platycodi Radix
  Platycodin A,C,D,D2, Polygalacin D,D2, Inulin, Betulin α-Spinasterol, α-Spinasterol glucoside, Stigmast-7-enol, Alismatis Rhizoma
  Alisol A,B, Lecithin, Alisol B monoacetate, Choline, Alisol C monoacetate, Alisol A monoacetate, Tab. 2-4

Myristicae Semen
  (+)-Camphene, (+)-Linalool, Safrole, Eugenol, Xylan, Saponin, Myristicin, (+)-α-Pinene, (+)-β-Pinene, (+)-Limonene, Furfural, (+)-Borneol, Geraniol, α-Terpineol, Myristin olein, Pentosan, Pectin, Lipase, Amomi Cardamomi Fructus
  (+)-Camphor, (+)-Borneol, Humulene epoxide, 1,8-Cineole, α-Pinene, β-Pinene, Caryophyllene, Myrcene, Babinene, Btiulene, Carvone, Artemisiae Capillaris Herba
  capillin, capillene, capillone, capiliarin, Norcapillene, capillanol Chrysanthemum
  (−)-α-Bisabolol, α-Farnesene, Matricin, Matricarin, Chamazulene, Cinae Flos
  (−)-α-Pinene, Terpinene, Terpineol, Carvacrol, α-Thujone, (−)-Camphor, Saussureae Radix
  Aplotaxene, Costic acid, Costunolide, Costus lactone, Camphene, Dehydrocostus lactone, Dihydrocostus lactone, Phellandrene, α-Ionone, β-Ionone, α-Costol, Valerianae Radix
  (+)-Bornylisovalerate, Bornylacetate, Kessane, (−)-Campehne, (+,−)-Limonene, α-Terpineol, α-Kessylalcohol, α-Pinene α-Kessylalcohol acetate, Kessanol, Kessoglycol, Valeranone, Fauronyl acetate, Cryptofauronol, Kanokonyl acetate, Linalool, β-Pinene, Kanokonol, Menthae Herba
  (−)-Menthol, Acetyllmenthone, (−)-Menthone, (−)-Limonene, (+)-Menthol Pulegone, Piperitone, Isomenthone, Camphene, 3-Octanol, γ-Hexenyl, Penylacetate, α-Pinene, Menthenone Perillae Herba
  (−)-Perillaldehyde, (+)-Limonene, α-Pinene, Periltaketone, naginataketone, egomaketone Tab. 3-1

Schizonepetae Herba
  (+)-Menthone, (±)-Menthonel, (+)-Limonene, (−)-Pulegone

Corni Fructus
  Oleanolic acid, Ursolic acid, Isoterchebin, Tellimagrandin I, Tellinagrandin II, Gemin D, Cornusiin A, Cornusiin B, Triogalloyl-β-D-glucose, Foeniculi Fructus Anethole, Estragole, (+)-α-Pinene, (+)-Fenchone, (±)-Limonene, Anisalddehyde Caryophylli Flos Eugenol, Eugenol acetate, Eugenol salicylate, Vanillin, Methyl salicylate, β-Caryophyllene, Humulene, Chavicol, Methyl amylketone, α-Ylangene Eucalypti Folium 1,8-Cineole, P-Cymene, Terpineol, Cuminal, Phellandral, Pinene Sengae Radix Methyl salicylate, Senegin-I, Senegin-II, Senegin-III, Senegin-IV Zanthoxyli Fructus Geraniol, Limonene, Cumic alcohol Asari Herba cum Radiae Euctarvone, Safrole, Methyleugenol, Elemicin, Asaricin, β-pinene, (+)-borneol, Croweacin Piperis Fructus (−)-α-Phellandrene, β-pinene, Linalool Houttuyniae Herba Decanoylacetaldehyde, Methylnonyl ketone, Laurinaldehyde Schizandrae Fructus Citral, α-Chamigrene, β-Chamigrene, Chamigrene, Sesquicarene, β-Chamigrenal Tab. 3-2

Magnoliae Flos

Methylchavicol, Camphor, 1,8-cincole, p-cymene

Lupuli Strobilus

α-humulene, β-humulene, Humuladienone, α-corocalene, Meta-camphorene, Paracamphorene, Myrcene Alpiniae Fructus Nootkatone, Zingiberene, Zingiberol, α-humulene Amomi Semen (+)-borneol, Bornylacetate, N-eroldiol Curcumae Tuber Turmerone, (+)-arturmerone, Zingiberne, (+)-α-phellandrene Zedoriae Rhizoma Curzerenone, Curdione, Curcolone, Furanodienone, Furanogermenone, 1,4-cineole, Zederone, Curcumol Cyperi Rhizoma Cyperol, α-Cyperone, Cyperene, Cyperotundone, Cyperolone, Sugenolacetate, Kobusone Croci Stigma Safranal Polygalae Radix Onjisaponin A-G A=senegin IV, B=senexin III, Prosenegeni, Tenuifolin, Senegenin, Astragali Radix Astragaloside I–VIII, Soyasaporin I Achyranthis Radix Oleanalic acid glycoside Anemarrhenae Rhizoma Timosaponin A-I, Timosaponin A-III, Neogitogenin glycosides, Markogernin,

What is claimed:

1. A transdermal formulation for providing antiviral effect in dermis or epidermis, comprising:

(a) 0.01 to 30 weight percent of antiviral drug selected from the group consisting of ACV (Acyclovir), DDA (2',3'-Dideoxyadnosine), DHPG (Ganciclovir), Vidarabine (Ara-A), and Amantadine;

(b) oleanolic acid and at least 2 weight percent of glycyrrhizin;

(c) a pharmaceutically acceptable vehicle so as to form a formulation that can be applied trandermally to a human body.

2. A method of trandermally providing antiviral effect in dermis or epidermis to a human body in need thereof, comprising the steps of:

(a) preparing a transdermal formulation which comprises:

(i) 0.01 to 30 weight percent of antiviral drug selected from the group consisting ACV (Acyclovir), DDA (2',3'-Dideoxyadnosine), DHPG (Ganciclovir), Vidarabine (Ara-A), and Amantadine;

(ii) oleanolic acid and at least 2 weight percent of glycyrrhizin;

(iii) a pharmaceutically acceptable vehicle so as to form a formulation in the form of an ointment, suspension, gel, or solution that can be applied trandermally to a human body; and (b) applying a patch to or spraying said transdermal formulation onto a human body.

* * * * *